United States Patent [19]

Horner et al.

[11] Patent Number: 4,465,787

[45] Date of Patent: Aug. 14, 1984

[54] RUTHENIUM-ON-CHARCOAL AND RUTHENIUM-ON-CARBON BLACK HYDROGENATION CATALYSTS, THEIR PREPARATION AND THEIR USE FOR SELECTIVE HYDROGENATION OF UNSATURATED CARBONYL COMPOUNDS

[75] Inventors: Michael Horner, Neustadt; Matthias Irgang, Heidelberg, both of Fed. Rep. of Germany

[73] Assignee: BASF Aktiengesellschaft, Ludwigshafen, Fed. Rep. of Germany

[21] Appl. No.: 397,781

[22] Filed: Jul. 13, 1982

[30] Foreign Application Priority Data

Aug. 4, 1981 [DE] Fed. Rep. of Germany ....... 3130805

[51] Int. Cl.³ ........................ B01J 23/89; B01J 23/46; C07C 29/14; C07B 1/00
[52] U.S. Cl. ................................... 502/185; 260/690; 568/881
[58] Field of Search ................ 252/447; 502/185, 406

[56] References Cited

U.S. PATENT DOCUMENTS

| | | | |
|---|---|---|---|
| 3,784,675 | 1/1974 | Kobylinski et al. | 423/213.5 |
| 3,912,787 | 10/1975 | Nowack et al. | 585/270 |
| 4,212,824 | 7/1980 | Seagraves | 252/447 |

FOREIGN PATENT DOCUMENTS 642299  6/1962  Canada ................. 252/447

Primary Examiner—P. E. Konopka
Attorney, Agent, or Firm—Oblon, Fisher, Spivak, McClelland & Maier

[57] ABSTRACT

Ruthenium-on-charcoal and ruthenium-on-carbon black catalysts, containing from 0.1 to 5% by weight of iron, for the preparation of olefinically unsaturated alcohols by selective hydrogenation of the corresponding $\alpha,\beta$-unsaturated carbonyl compounds in the liquid phase are prepared by modifying the catalyst with iron only after it has been impregnated with the ruthenium compound, and reducing the catalyst with hydrogen at from 400° to 600° C., with thorough mixing.

The catalysts according to the invention are particularly useful for improving the industrially difficult hydrogenation of citral to give the sought-after fragrances geraniol and nerol.

10 Claims, No Drawings

RUTHENIUM-ON-CHARCOAL AND RUTHENIUM-ON-CARBON BLACK HYDROGENATION CATALYSTS, THEIR PREPARATION AND THEIR USE FOR SELECTIVE HYDROGENATION OF UNSATURATED CARBONYL COMPOUNDS

BACKGROUND OF THE INVENTION

1. Field of the Invention:

The present invention relates to ruthenium-on-charcoal supported catalysts modified with iron, their preparation and their use for the preparation of olefinically unsaturated alcohols by selective hydrogenation of the corresponding carbonyl compounds in the liquid phase in the presence of a noble metal catalyst and of a tertiary amine.

2. Description of the Prior Art

German Laid-Open Application DOS 2,934,251 discloses a process for the preparation of olefinically unsaturated alcohols, in particular geraniol and nerol (E- and Z-3,7-dimethyl-octa-2,6-dien-1-ol), by selective hydrogenation of the corresponding α,β-unsaturated carbonyl compounds in the liquid phase in the presence of a noble metal catalyst, e.g. a ruthenium, rhodium, osmium, iridium or platinum catalyst, and of a tertiary amine. As can be seen from the introduction to the description in the above Laid-Open Application, industrial preparation of the said unsaturated alcohols is fairly difficult, since large amounts of the very expensive noble metal catalysts are necessary, the catalysts must be pretreated in an expensive manner, the activity of the catalyst frequently decreases relatively rapidly, and/of the selectivity of the catalysts leaves much to be desired. The presence of a tertiary amine in the reaction mixture, as proposed in the above Laid-Open Application, substantially increases the selectivity of the reaction and also improves the activity of the catalyst over long operating periods with relatively little expense or technical effort. However, even this process has the following disadvantages, especially if the inexpensive, commercially available ruthenium catalysts are used:

1. The selectivity of the ruthenium catalysts is still not completely satisfactory, especially for the synthesis of geraniol.

2. The hydrogenation does not stop selectively at the alcohol stage after 1 mole of hydrogen has been taken up per mole of aldehyde, and this increases the formation of the perhydrogenation products citronellol and tetrahydrogeraniol, which are difficult to remove by distillation, and thus obstructs preparation of the unsaturated alcohols, which are sought-after scents, in a pure form.

3. The space/time yields in the high pressure range are still unsatisfactory.

4. The hydrogenation times in the pressure range <50 bar are too long when small amounts of catalyst are employed.

It is an object of the present invention to provide, for the process of German Laid-Open Application DOS No. 2,934,251, which is in itself very advantageous, a catalyst which is based on ruthenium, by far the cheapest platinum metal, and substantially avoids the disadvantages described in respect of hydrogenation activity and selective stopping of the hydrogenation of the unsaturated aldehydes.

Ruthenium-on-active-charcoal catalysts are produced industrially and are commercially available. The prior art on these catalysts is described in the monograph by J. D. Anderson, "Structure of Metallic Catalysts" (London, New York, San Francisco 1975). There if no more recent work containing data for the preparation of Ru-on-C catalysts.

Starting materials for Ru catalysts are, inter alia, $RuCl_3$ or $RuCl_3.aq.$, $(NH_4)_2[RuCl_6]$ and $(NH_4)_2[RuCl_5.H_2O]$.

Various methods are known for the preparation of the catalysts. The most important are impregnation of the carrier with a soluble Ru compound, cation exchange on suitable carriers, starting from $[Ru(NH_3)_4(NO)(OH)]^{2+}$ or $[Ru(NH_3)_6]^{3+}$, and precipitation of sparingly soluble Ru compounds onto the surface of the carrier.

The catalyst is additionally reduced, at the same time or subsequently. Temperatures from 250° to 500° C. are given for reduction with hydrogen (Orito, Y. and Sabi, O., Yoki Gosei Kagaku Kyokaishi 30 (1972) 6, 563–565).

SUMMARY OF THE INVENTION

We have found that the object of the invention is achieved by a ruthenium-on-charcoal or a ruthenium-on- carbon black catalyst for the preparation of olefinically unsaturated alcohols by selective hydrogenation of the corresponding unsaturated carbonyl compounds in the liquid phase, which, in addition to from 0.1 to 10% by weight, preferably from 1 to 6% by weight, of ruthenium on a carbon carrier, preferably on active charcoal, contains from 0.1 to 5% by weight, preferably from 0.5 to 1.5% by weight, of iron and is prepared by a process which involves (a) modifying the catalyst with iron only after it has been impregnated with the ruthenium compound and (b) reducing the catalyst with hydrogen at from 400° to 600° C., with thorough mixing, in particular a ruthenium-on-charcoal catalyst which has been prepared by reduction with hydrogen at from 500° to 600° C.

DETAILED DESCRIPTION OF THE INVENTION

The present invention also relates to a process for the preparation of these ruthenium-on-charcoal catalysts for the preparation of olefinically unsaturated alcohols, by impregnating the carbon carrier with a ruthenium compound and then reducing the catalyst with hydrogen, wherein (a) the catalyst is modified with from 0.1 to 5% by weight, preferably from 0.5 to 1.5% by weight, of iron after it has been impregnated with the ruthenium compound, and (b) the catalyst is reduced with hydrogen at from 400° to 600° C., with thorough mixing, in particular a process wherein the catalyst is reduced with hydrogen at from 500° to 600° C.

The present invention furthermore relates to the use of a ruthenium-on-charcoal or a ruthenium-on-carbon black catalyst, as described above, for the preparation of an unsaturated alcohol of the general formula Ia

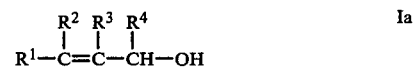

where $R^1$ is hydrogen or an organic radical and $R^2$, $R^3$ and $R^4$ are hydrogen or $C_1$-$C_4$-alkyl, by selective hydrogenation of the corresponding α,β-unsaturated carbonyl compound IIa $$R^1-\underset{|}{C}=\underset{|}{C}-\underset{|}{C}=O \qquad \text{IIa}$$
$$\phantom{R^1-}R^2\phantom{=}R^3\phantom{-}R^4$$

in the liquid phase in the presence of a tertiary amine.

In addition to ruthenium and a carbon carrier, such as active charcoal or carbon black, preferably active charcoal, the hydrogenation catalyst according to the invention contains from 0.1 to 5% by weight, preferably from 0.5 to 1.5% by weight, of iron. Such a modification with iron has not previously been disclosed for Ru-on-C catalysts.

It is known that the selectivity for hydrogenation of the formyl group of cinnamaldehyde over a platinum catalyst can be improved if other catalyst components are also used, e.g. iron and zinc (Belgian Patent No. 837,057), iron and silver (U.S. Pat. No. 3,284,517) or cobalt (German Laid-Open Application DOS No. 2,412,517). However, for economic reasons, the use of very expensive noble metals such as platinum is advantageous only if the catalyst can be recycled to the reaction zone without substantial changes in catalytic activity. In fact, in the above catalyst systems, the use of other catalyst components causes a noticeable drop in catalyst activity, which reduces the industrial usefulness of this hydrogenation process (cf. German Laid-Open Application DOS No. 2,650,046, page 3). It is therefore very surprising that, when a ruthenium catalyst is used, which is the most advantageous platinum metal since it is by far the cheapest, a selectivity-increasing modification with iron can be achieved which, far from decreasing the catalyst activity, actually increases it, as is shown, for example, by the fact that the use of the same amount of catalyst can drastically shorten hydrogenation times (cf. Examples 3, 7, 10 and 11 compared with Comparative Examples 3C, 7C, 10C and 11C). The hydrogenation times can even be shorter than those requiring 2.5 times the amount of an unmodified catalyst (c.f. 4 in comparison with 4C). While the catalyst activity is increased, the selectivity is improved and the hydrogenation can be selectively stopped. Examples 5 and 9 furthermore show that the catalysts according to the invention also permit economical hydrogenation times under pressures in the region of 20 bar, while the same amounts of commercially available catalysts permit only incomplete hydrogenation under these pressures.

It has moreover been found, surprisingly, that the modification, according to the invention, with iron also gives the ruthenium-on-C catalysts a long life, which is manifested by the high number of production batches which can be hydrogenated in the same advantageous manner with the same catalyst bed (cf. Example 6 in comparison with Example 4).

The above improvements to the catalyst by modification with the iron can, however, only be achieved if certain measures are taken during the preparation. Thus, simultaneous impregnation of the carbon carrier with ruthenium chloride solution and iron chloride solution or iron nitrate solution proves to be ineffective, and the resulting catalyst has a lower activity than the unmodified sample. Surprisingly, improved catalysts are obtained only if the modification with iron is not carried out until after the impregnation with the ruthenium compound.

Advantageously, the ruthenium is applied to the carbon carrier in a conventional manner, and the resulting catalyst intermediate is dried, and mixed with iron oxide or iron in the form of iron oxide powder or iron powder. The catalyst intermediate is reduced with hydrogen during or after the mixing operation.

The reduction conditions also have a marked influence on the catalyst properties. Thus, it has been found that an Ru-on-C catalyst which has been reduced at below 400° C., which is generally the case for reduction of a noble metal catalyst, has a substantially lower activity. The highest hydrogenation activities of Ru-on-C catalysts are achieved with catalysts which have been reduced with hydrogen at from 500° to 600° C. This temperature is significantly above the hitherto conventional reduction temperature for a noble metal-on-C catalyst.

Moreover, it is necessary to mix the catalyst thoroughly during reduction with hydrogen. All attempts to produce a highly active Ru-on-C catalyst by reduction in a stationary bed or in a fixed bed have failed. In contrast, good results are achieved on reduction in a rotary tube oven.

The above measures are evidently essential to produce a suitable structure of the Ru/Fe crystallites on or in the active charcoal particles.

DESCRIPTION OF THE PREFERRED EMBODIMENTS

The statements below further describe the catalysts according to the invention:

The catalysts according to the invention in general contain from 0.1 to 10% by weight of ruthenium on a carbon carrier, such as active charcoal or carbon black, preferably on active charcoal. Very good results have been obtained with catalysts which, like most commercially available noble metal-on-charcoal catalysts, contain 5% of ruthenium on active charcoal.

From 0.0001 to 0.1% by weight, in particular from 0.001 to 0.1% by weight, of ruthenium, based on the metal content and on the amount of starting compound II, is preferably used.

Depending on the carbon carrier used for the preparation, the BET surface area of the catalyst is from about 600 to 900, preferably from about 700 to 800, m²/g for active charcoal and from about 300 to 700 m²/g for carbon black. The particle size of the Ru crystallites is from 2 to 5 nm, and thus corresponds to the values for Ru-on-C catalysts given in the Literature. The Ru is in elementary form, as can be seen from ESCA measurements. (ESCA=electron spectroscopy for chemical analysis). Since the catalyst may be pyrophoric in the presence of air, it is advantageously handled in powder form containing 50% of H₂O. This powder is still freeflowing, but does not dust and is not pyrophoric. In the present application, the % by weight data for the ruthenium and iron in the catalyst are always based on the dry weight of catalyst.

The particular field of use of the catalysts according to the invention is the preparation of an unsaturated alcohol of the general formula Ia $$R^1-\underset{|}{C}=\underset{|}{C}-\underset{|}{CH}-OH \qquad \text{Ia}$$
$$\phantom{R^1-}R^2\phantom{=}R^3\phantom{-}R^4$$

where $R^1$ is hydrogen or an organic radical and $R^2$, $R^3$ and $R^4$ are hydrogen or $C_1$-$C_4$-alkyl, by selective hydrogenation of an α,β-unsaturated carbonyl compound IIa

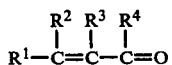

IIa under the reaction conditions described in German Laid-Open Application DOS No. 2,934,251.

In this context also, the process according to the invention is of particular importance for the hydrogenation of citral (compound IIb)

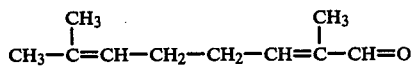

IIb to give geraniol or nerol (compounds E-Ib or Z-Ib)

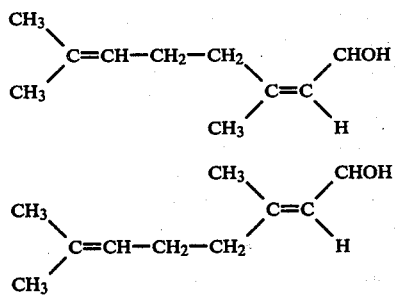

which is known to cause industrial problems since perhydrogenation and isomerization occur as competing reactions.

However, the process can equally well be used for the other compounds IIa, in which case it usually also provides the above advantages compared with the conventional processes, and almost always does so in the case of those compounds IIa conforming to the above definition in which, because of their conjugation to the carbonyl group, the olefinic double bonds are particularly easily hydrogenated.

In principle, $R^1$ in the compounds IIa can be any desired radical. If this radical contains other olefinic double bonds, these are not attacked. Examples of $R^1$ are alkyl and alkenyl of 1 to 20 carbon atoms and aromatic radicals, such as phenyl. These radicals can in turn carry, for example, alkyl, alkoxy, carbalkoxy, acyl, hydroxyl, carboxyl, nitrile, amino or halogen as substituents. Since the principle of the process is not affected by the type of substituents $R^1$, $R^2$ and $R^3$, separate listing of the possible starting compounds IIa is superfluous. This also applies generally to the starting compounds II, the essential criterion of which is the presence of one or more olefinic double bonds which are not or not noticeably attacked during hydrogenation of the carbonyl group. The rest of the chemical nature of the compounds is of no importance, but in practice they are usually straight-chain or branched mono- or polyunsaturated alkenals or alkenols of 4 to 40 carbon atoms.

The carbonyl compounds of general formula IIa are hydrogenated over a catalyst according to the invention in the presence of a tertiary amine.

In principle, from observations made hitherto, any tertiary amine is suitable, so that its chemical nature is of no consequence as long as it cannot otherwise react with the reactants on the basis of functional groups. Examples of suitable amines are aliphatic tertiary amines of 3 to 30 carbon atoms in total, e.g., in particular, trimethylamine, triethylamine, triethanolamine and trihexylamine, tertiary cyclic amines, e.g. N-methylpiperidine, N-methylmorpholine and N,N'-dimethylpiperazine, aliphatic-cycloaliphatic tertiary amines, e.g. N,N-dimethylcyclohexylamine, aliphatic-araliphatic tertiary amines, e.g. N,N-dimethylbenzylamine, aliphatic-aromatic tertiary amines, e.g. N,N-dimethylaniline, and heterocyclic-aromatic tertiary amines, e.g. pyridine and quinoline.

For economic reasons, the cheapest amine having a boiling point either significantly below or significantly above that of the process product will be used, since in these cases either the amine or the process product can easily be distilled off from the reaction mixture.

The amount of amine is preferably from 25 to 40% by weight of the starting material of compounds II.

It is advisable to carry out the reaction in the presence of a solvent. The amount of solvent is generally from 10 to 300, preferably from 25 to 150%, by weight of compound II, and suitable solvents are inert liquids in which both compounds I and II and the tertiary amine used are soluble. Examples include the tertiary amines themselves and, in addition, alcohols, such as methanol and ethanol, ethers, acetone and hydrocarbons which are liquid under the reaction conditions, such as hexane and cyclohexane. Methanol is preferred, especially if trimethylamine is used as the base, since in this case working up of the reaction mixture is particularly simple.

The hydrogenation is otherwise carried out in a conventional manner, i.e. at from 20° to 150° C. and under a pressure of from 20 to 200 bar, if less than 0.01% by weight of catalyst metal (based on II) is used, and under a pressure of from 1 to 150 bar if the amount of catalyst is greater than 0.01% by weight.

The preparation of unsaturated alcohols by selective hydrogenation of the corresponding α,β-unsaturated carbonyl compounds in the presence of amines can be substantially improved with the aid of the catalysts according to the invention. Compared with the conventional procedure, substantially increased space/time yields are obtained, and in addition the selectivity for the process products is improved and is maintained at its original high level over long operating periods, which is of particular importance for fragrances and aromatics, e.g. citronellal, since the yield of the desired process products drops substantially if preparation of the product in a pure form is carried out at economically acceptable expense.

EXAMPLE 1

A Preparation of the catalyst according to the invention 1,000 g of pulverulent active charcoal (BET surface area: 750 m²/g) are impregnated with a solution of 140 g of ruthenium chloride hydrate in 2,000 g of distilled water, and the components are mixed thoroughly. The resulting material is dried at from 80° to 90° C. and is then mixed, in the dry state, with 15 g of $Fe_2O_3$ powder.

The catalyst product thus obtained is reduced in a gas-tight rotary tube oven. The contents of the oven are flushed with a stream of nitrogen of 50 l/h for one hour and are then heated up to 500° C. in a stream of hydrogen of 100 l/h in the course of 2 hours. After reduction has been carried out for 3 hours, the stream of hydrogen is changed to $N_2$ and the heating is switched off. After the oven has cooled, the product is removed and introduced into 1,000 g of distilled water, so that the finished catalyst has a water content of 50% by weight.

The dry catalyst contains 5% by weight of ruthenium and 1% by weight of Fe.

B Preparation of the catalyst according to the invention
with reduction of the catalyst at from 500° to 600° C.

The procedure described in A is followed, but, after being flushed with a stream of nitrogen, the contents of the rotary tube oven are heated up to 600° C. in a stream of hydrogen of 100 l/h in the course of 2 hours and are then reduced for 3 hours.

C COMPARATIVE EXAMPLE

Preparation of an Fe-modified Ru-on-C catalyst by impregnating the active charcoal simultaneously with a ruthenium salt solution and an iron salt solution and reducing the catalyst intermediate in a fixed bed.

A solution of 140 g of ruthenium chloride hydrate and 40 g of $FeCl_2.4H_2O$ in 2,000 g of distilled water is added to 1,000 of pulverulent active charcoal (BET surface area: 750 m$^2$/g) in a mixer, and the components are mixed thoroughly for 30 minutes. The resulting material is dried at from 80° to 90° C.

The catalyst intermediate thus obtained is introduced into a gas-tight, vertical reduction oven which permits gassing of the catalyst material via a heat-resistant perforated sheet. The contents of the oven are flushed with a stream of nitrogen of 50 l/h for one hour and are then heated up to 500° C. in a stream of hydrogen of 100 l/h in the course of 2 hours. After reduction has been carried out for 3 hours, the stream of hydrogen is changed to $N_2$ and the heating is switched off. After cooling, the catalyst is removed.

The catalyst contains 5% by weight of Ru and 1% by weight of Fe.

D COMPARATIVE EXAMPLE

Preparation of an Fe-modified Ru-on-C catalyst by impregnating the active charcoal simultaneously with a ruthenium salt solution and an iron salt solution and reducing the catalyst intermediate, with thorough mixing.

The catalyst intermediate obtained by a method similar to that described in Comparative Example 1C is reduced in a gas-tight rotary tube oven. The contents of the oven are flushed with a stream of nitrogen of 50 l/h for one hour and are then heated up to 500° C. in a stream of hydrogen of 100 l/h in the course of 2 hours. After reduction has been carried out for 3 hours, the stream of hydrogen is changed to $N_2$ and the heating is switched off. After the oven has cooled, the product is removed and is introduced into 1,000 g of distilled water, so that the finished catalyst has a water content of 50% by weight.

The dry catalyst contains 5% by weight of ruthenium and 1% by weight of iron.

EXAMPLES 2-6

Partial hydrogenation of citral

In each case 45 g of pure citral are hydrogenated under various conditions, a supported catalyst, which has active charcoal as the carrier and contains 5% by weight, based on the dry weight, of ruthenium and the amount of iron given in Table 1, being used in each case. The catalyst for each of Examples 2A-2D is the catalyst prepared in Examples 1A-1D respectively. The catalyst for Examples 3, 4, 5 and 6 is prepared by a method similar to that described in Example 1B, and the catalyst for Examples 3(C) and 4(C) is a commercially available Ru-on-C catalyst. The particular reaction conditions and the results of the individual experiments are summarized in Table 1 which follows. Comparative experiments are Labeled (C). The yields of process products were determined by gas chromatography, and the yields of residue were determined gravimetrically.

TABLE 1

| Experiment No. | Catalyst Ruthenium [% by weight][1] | Catalyst Iron [% by weight][2] | Methanol [g] | Amine[3] [g] | Pressure [bar] | Temperature [°C.] | Time [hours] | Conversion[1] [%] | Yield[4] Geraniol/nerol | Yield[4] Citronellol | Residue |
|---|---|---|---|---|---|---|---|---|---|---|---|
| 2A | 0.04 | 0.56 | 32 | 16 | 50 | 100 | 6 | 100 | 96.5 | 2.3 | 1 |
| 2B | 0.04 | 0.61 | 32 | 16 | 50 | 100 | 5 | 100 | 96.2 | 3.1 | 1 |
| 2C(C) | 0.04 | 1.0 | 32 | 16 | 50 | 100 | 24 | 99.2 | 95 | 4.2 | 1 |
| 2D(C) | 0.04 | 0.84 | 32 | 16 | 50 | 100 | 21 | 98.7 | 94 | 5.3 | 1 |
| 3 | 0.02 | 0.56 | 32 | 16 | 100 | 50 | 4 | 100 | 96.2 | 2.8 | 1 |
|  |  |  |  |  |  |  | 5 | 100 | 95.8 | 3.2 | 1 |
| 3(C)[5] | 0.02 | — | 32 | 16 | 100 | 50 | 6 | 100 | 93 | 6.0 | 1 |
|  |  |  |  |  |  |  | 7 | 100 | 91.5 | 7.5 |  |
| 4 | 0.04 | 0.56 | 32 | 16 | 50 | 100 | 7 | 100 | 96.4 | 2.6 | 1 |
|  |  |  |  |  |  |  | 9 | 100 | 96.0 | 3.0 |  |
| 4(C)[6] | 0.1 | — | 32 | 16 | 50 | 100 | 8 | 100 | 93.4 | 6.1 | 1 |
|  |  |  |  |  |  |  | 9 | 100 | 91.8 | 7.2 |  |
| 5 | 0.04 | 0.56 | 32 | 16 | 20 | 100 | 15 | 99.2 | 96.3 | 3.0 | 1 |
| 6 | 0.04[7] | 0.56 | 32 | 16 | 50 | 100 | 8 | 99.8 | 96.1 | 2.8 | 1 |

[1] based on the aldehyde employed
[2] based on the weight of dry catalyst
[3] trimethylamine
[4] based on aldehyde reacted
[5] corresponds to Example 3 from German Laid-Open Application DOS 2,934,251
[6] corresponds to Example 16 from German Laid-Open Application DOS 2,934,251
[7] catalyst recycled 7 times

EXAMPLES 7-9

Partial hydrogenation of citronellal

In each case 40 g of pure citronellal are hydrogenated under various conditions, a supported catalyst, which has active charcoal as the carrier and contains 5% by weight, based on the dry weight, of ruthenium and the amount of iron given in Table 2, being used in each case. The catalyst for Examples 7, 8 and 9 is prepared by a method similar to that described in Example 1B. The catalyst for Example 7(C) is a commercially available Ru-on-C catalyst. The reaction conditions and the results are summarized in Table 2 which follows.

TABLE 2

| Experiment No. | Catalyst Ruthenium [% by weight][1] | Iron [% by weight][2] | Methanol [g] | Amine [g] | Pressure [bar] | Temperature [°C.] | Time [hours] | Conversion[1] [%] | Citronellol [%] | Yield[4] 3,7-Dimethyl-octanol [%] | Isopa-legol [%] | Residue |
|---|---|---|---|---|---|---|---|---|---|---|---|---|
| 7 | 0.02 | 0.56 | 32 | 16 | 50 | 100 | 6 | 99.8 | 98.2 | 0.3 | 0.3 | 1 |
|   |      |      |    |    |    |     | 8 | 99.9 | 97.9 | 0.6 | 0.3 |   |
| 7(C)[5] | 0.02 | — | 32 | 16 | 50 | 100 | 9 | 100 | 97.6 | 1.0 | 1.0 | 1 |
|   |      |   |    |    |    |     | 10 | 100 | 94.3 | 3.2 | 1.0 |   |
| 8 | 0.02 | 0.56 | 32 | 16 | 100 | 100 | 3.5 | 99.7 | 98.0 | 0.6 | 0.2 | 1 |
|   |      |      |    |    |     |     | 5 | 100 | 97.4 | 1.0 | 0.2 |   |
| 9 | 0.04 | 0.56 | 32 | 16 | 20 | 100 | 12 | 99.7 | 98.1 | 0.5 | 0.3 | 1 |

[1]based on the aldehyde employed
[2]based on the weight of the dry catalyst
[3]trimethylamine
[4]based on the aldehyde reacted
[5]corresponds to Example 13 in Table 2 of German Laid-Open Application DOS 2,934,251

EXAMPLES 10 and 11

Partial hydrogenation of various α,β-unsaturated aldehydes 40 g of each of the aldehydes mentioned in Table 3 are hydrogenated under the conditions given in this Table, a supported catalyst, which has active charcoal as the carrier and contains 5% by weight, based on the dry weight, of ruthenium and the amount of iron given in Table 3, being used in each case. The catalyst for Examples 10 and 11 is prepared by a method similar to that described in Example 1B, and the catalyst for Examples 10(C) and 11(C) is a commercially available Ru-on-C catalyst.

TABLE 3

| Experiment No. | Aldehyde | Catalyst Ruthenium [% by weight][1] | Iron [% by weight][2] | Methanol [g] | Amine[3] [g] | Pressure [bar] | Temperature [°C.] | Time [hours] | Conversion[1] [%] | Yield[4] Alcohol | | Residue [%] |
|---|---|---|---|---|---|---|---|---|---|---|---|---|
| 10 | 3,7-dimethyl-nona-2,6-dien-1-al | 0.02 | 0.56 | 32 | 16 | 50 | 100 | 6 | 99 | 3,7-dimethyl-nona-dien-1-ol | 96 | 1 |
| 10(C)[5] | 3,7-dimethyl-nona-2,6-dien-1-al | 0.02 | — | 32 | 16 | 50 | 100 | 9 | 99 | 3,7-dimethyl-nona-dien-1-ol | 94 | 1 |
| 11 | 3-methyl-croton-aldehyde | 0.02 | 0.56 | 32 | 16 | 50 | 100 | 7 | 99 | 3-methyl-but-2-en-1-ol | 97 | 1 |
| 11(C)[6] | 3-methyl-croton-aldehyde | 0.02 | — | 32 | 16 | 50 | 100 | 12 | 98 | 3-methyl-but-2-en-1-ol | 95 | 1 |

[1]based on aldehyde employed
[2]based on the weight of dry catalyst
[3]trimethylamine
[4]based on aldehyde reacted
[5]corresponds to Example 7 in Table 3 of German Laid-Open Application DOS 2,934,251
[6]corresponds to Example 4 in Table 3 of German Laid-Open Application DOS 2,934,251

We claim:

1. A process for the preparation of a catalyst, comprising:
   impregnating a charcoal or carbon black catalyst with a ruthenium compound;
   modifying said ruthenium impregnated catalyst in the dried state by mixing with the powder of an iron compound; and
   reducing said iron modified catalyst with hydrogen at 400° C. to 600° C. while mixing.

2. A process for the preparation of a catalyst as claimed in claim 1, wherein the content of ruthenium is between 0.1 to 10% by weight.

3. A process for the preparation of a catalyst as claimed in claim 2, wherein the content of iron is between 0.1 to 5% by weight.

4. A process for the preparation of a catalyst as claimed in claim 3, wherein the content of iron is between 0.5 to 1.5% by weight.

5. A process for the preparation of a catalyst as claimed in claim 1 wherein the hydrogenation is carried out as a temperature between 500° and 600° C.

6. A charcoal or carbon black catalyst prepared by a process comprising:
   impregnating said charcoal or carbon black catalyst with ruthenium compound;
   modifying the ruthenium-impregnated catalyst in the dried state by mixing with the powder of an iron compound; and reducing said iron modified catalyst with hydrogen at 400° C. to 600° C. with thorough mixing.

7. A charcoal or carbon black catalyst as claimed in claim 6, wherein the content of ruthenium is between 0.1 and 10% by weight.

8. A charcoal or carbon black catalyst as claimed in claim 6 wherein the content of iron is between 0.1 to 5% by weight.

9. A charcoal or carbon black catalyst as claimed in claim 6 wherein the content of iron is between 0.5 and 1.5% by weight.

10. A charcoal or carbon black catalyst as claimed in claim 6 wherein said catalyst is reduced with hydrogen at between 500° and 600° C.

* * * * *